US006231622B1

(12) United States Patent
Chassot et al.

(10) Patent No.: US 6,231,622 B1
(45) Date of Patent: May 15, 2001

(54) DYE COMPOSITIONS, ESPECIALLY FOR DYEING HAIR, CONTAINING INDANE DERIVATIVE COMPOUNDS

(75) Inventors: Laurent Chassot, Praroman; Laurence Descloux, Lovens, both of (CH)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/421,800

(22) Filed: Oct. 20, 1999

(30) Foreign Application Priority Data

Nov. 13, 1998 (DE) ................................. 198 52 337

(51) Int. Cl.$^7$ .................................................. A61K 7/13
(52) U.S. Cl. ........................... 8/405; 8/404; 8/428; 8/603
(58) Field of Search .............................. 8/404, 405, 428, 8/636, 603, 435; 558/426; 585/27

(56) References Cited

U.S. PATENT DOCUMENTS 5,942,359 * 8/1999 Kinoshita et al. ........................ 430/58

FOREIGN PATENT DOCUMENTS

| 30 09 833 | 10/1981 | (DE) . |
| 42 15 654 | 11/1992 | (DE) . |
| 45 17 855 | 12/1994 | (DE) . |
| 43 35 628 | 4/1995 | (DE) . |
| 1-009968 * | 1/1989 | (JP) . |

OTHER PUBLICATIONS

CAPLUS Abstract of JP 4–086,658, Konica K.K., Mar. 1992.*
CAPLUS Abstract of SU 325,839, Riga Polytechnic Institute, Feb. 1972.*

Patent Abstract of Japan vol. 13, No. 182, JP 01 009968 A (Smitomo), Jan. 13, 1989.

Chemical Abstracts, vol. 126, No. 16, Apr. 21, 1997, Columbus, Ohia, US, K, Belli: "Novel Monoazo Dieperse Dyes . . . ", BD. 44, NR. 1, pp. 49–52.

* cited by examiner

Primary Examiner—Caroline D. Liott
(74) Attorney, Agent, or Firm—Michael J. Striker

(57) ABSTRACT

The dye composition for fibers, especially keratin-containing fibers, contains at least one indane derivative compound of formula I, or a physiologically compatible, water-soluble salt thereof:

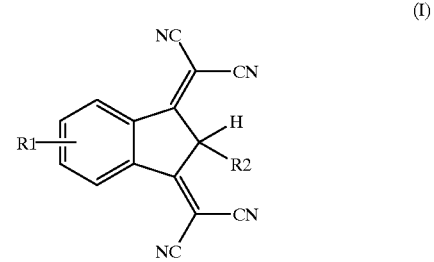

wherein R1 is hydrogen, a halogen atom, a cyano group, a hydroxy group, a $C_1$— to $C_4$— alkoxy group, a $C_1$— to $C_6$— alkyl group, a nitro group, an amino group, an alkylamino group, a dialkylamino group, a —C(O)H group, a —COOR3 group, a —SO$_2$R3 or a —C(O)CH$_3$ group, wherein R3 is hydrogen, phenyl or a $C_1$— to $C_6$— alkyl group; and R2 is hydrogen, a $C_1$— to $C_6$— alkyl group or a phenyl group.

13 Claims, No Drawings

DYE COMPOSITIONS, ESPECIALLY FOR DYEING HAIR, CONTAINING INDANE DERIVATIVE COMPOUNDS

BACKGROUND OF THE INVENTION

1. Field of the Invention

The present invention relates to a composition for dyeing fibers, especially keratin fibers, containing 1,3-bis-(dicyanomethylen)indane dyestuffs. The keratin fibers include wool, fur and human hair.

2. Prior Art

Two dyeing methods are generally employed for dyeing keratin-containing fibers. In the first method the color of the dyed keratin-containing fibers is produced with a so-called oxidative or permanent dye composition using a mixture of different coupler substances and developer substances and an oxidizing agent. Direct-dyeing (non-oxidative) dye compounds are added, as required, for rounding out the color properties or for producing special color effects. The second method involves the exclusive direct-dyeing dye compounds that are applied to the fibers in a suitable dye carrier. This method is simple to use, mild and characterized by minimal damage to the hair. The direct-dyeing dye compounds used in this latter method have a number of requirements. They must be toxicologically and dermatologically unobjectable and allow the production of colors in the desired intensity, which, among other things, presupposes sufficient water-solubility. Moreover good light-fastness, acid-fastness and friction- or rubbing-fastness is required.

Usually a combination of direct-dyeing (non-oxidative) dye compounds is required for keratin fibers. Since the selection of red-dyeing and blue-dyeing dye compounds that can be used in dye composition for keratin fibers, especially human hair, is limited, it has been necessary to expand the usable color palette.

SUMMARY OF THE INVENTION

It has now been found surprisingly that certain indane derivative compounds dye fibers, especially keratin fibers, an intense blue color.

The subject matter of the present invention is thus a composition for dyeing fibers, especially keratin fibers, which is characterized in that it contains at least one indane derivative compound of formula I or its physiologically compatible salt:

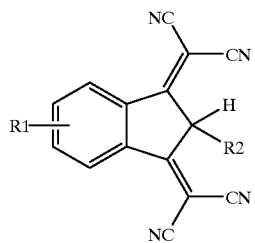

(I)

wherein the R1 and R2 groups, independently of each other, have the following significance:

R1 is hydrogen, a halogen atom, a cyano group, a hydroxy group, a $C_1$— to $C_4$— alkoxy group, a $C_1$— to $C_6$— alkyl group, a nitro group, an amino group, an alkylamino group, a dialkyl amino group, a —C(O)H group, a —COOR3 group, a —SO$_2$R3 or a —C(O)CH$_3$ group, wherein R3 is hydrogen, phenyl or a $C_1$— to $C_6$— alkyl group;

R2 is hydrogen, a $C_1$— to $C_6$— alkyl group or a phenyl group.

Preferred indane derivative compounds of formula I are those with R1=hydrogen or —CH$_3$ and R2=methyl, phenyl or especially hydrogen.

Alkali salts and ammonium salts, especially the ammonium salt, triethylammonium salt, sodium salt, calcium salt, N-methylmorpholinium salt, monoethanol ammonium salt, diethanolammonium salt and triethanol ammonium salt are suitable as the physiologically compatible salts of formula I.

The compound of formula I is present in the hair dyeing composition in a total amount of about 0.01 to 10 percent by weight, especially from 0.01 to 5 percent by weight.

The compound of formula I dyes keratin material an intense blue shade without the addition of other dye compounds. To obtain other color shades or tones additional conventional direct-dyeing dye compounds, especially nitro dye compounds, azo dye compounds or quinone dye compounds are added to the hair dye compositions of the invention, as well as basic, acid or neutral dye compounds alone or in mixtures with each other.

Suitable nitro dye compounds include 1,4-bis-[(2-hydroxyethyl)amino]-2-nitrobenzene, 1-(2-hydroxyethyl)amino-2-nitro-4-[di(2-hydroxyethyl)amino]-benzene (HC Blue No. 2), 1-amino-3-methyl-4-[(2-hydroxyethyl)amino]-6 -nitrobenzene (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl)amino]-2-nitrobenzene (HC Blue No. 11), 1-[(2,3-dihydroxypropyl)-amino]-4-[methyl-(2-hydroxyethyl)amino]-2-nitrobenzene (HC Blue No. 10), 1-[(2,3-dihydroxypropyl)amino]-4-[ethyl-(2-hydroxyethyl)-amino]-2-nitrobenzene hydrochloride (HC Blue No. 9), 1-(3-hydroxypropyl-amino)-4-[di(2-hydroxyethyl)amino]-2-nitrobenzene (HC Violet No. 2), 1-methyl-amino-4-[methyl-(2,3-dihydroxypropyl)amino]-2-nitrobenzene (HC Blue No. 6), 2-((4-Amino-2-nitrophenyl)amino)-5-dimethylaminobenzoic acid (HC Blue No. 13), 1-(2-aminoethylamino)-4-[di(2-hydroxyethyl)amino]-2-nitrobenzene, 1-amino-4-[(2-hydroxyethyl)amino]-2-nitrobenzene (HC Red No. 7), 2-amino-4,6-dinitrophenol, 4-amino-2-nitrodiphenylamine (HC Red No. 1), 1-amino-4-[di-(2-hydroxyethyl)amino]-2-nitrobenzene hydrochloride (HC Red No. 13), 1-amino-5-chloro-4-[(2-hydroxyethyl)amino]-2-nitrobenzene, 4-Amino-1-[(2-hydroxyethyl)-amino]-2-nitrobenzene (HC Red No. 3), 4-((2-hydroxyethyl)methylamino)-1-(methylamino)-2-nitrobenzene, 1-amino-4-((2,3-dihydroxypropyl)amino)-5-methyl-2-nitrobenzene, 1-amino-4-(methylamino)-2-nitrobenzene, 4-amino-2-nitro-1-((prop-2-en-1-yl)amino)-benzene, 4-amino-3-nitrophenol, 4-[(2-hydroxy-ethyl)amino]-3-nitrophenol, 1-[(2-aminoethyl)amino]-4-(2-hydroxy-ethoxy)-2-nitrobenzene (HC Orange No. 2), 4-(2, 3-dihydroxy-propoxy)-1-[(2-hydroxy-ethyl)amino]-2-nitrobenzene (HC Orange No. 3), 1-amino-5-chloro- 4-[(2, 3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxy-ethyl)amino]-4,6-dinitrophenol, 4-ethylamino-3-nitrobenzoic acid, 2-[(4-amino-2-nitrophenyl)amino]-benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 6-amino-3-((2-hydroxyethyl) amino)-2-nitropyridine, 3-amino-6-((2-hydroxyethyl) amino)-2-nitropyridine, 3-amino-6-(ethylamino)-2-nitropyridine, 3-((2-hydroxyethyl)amino)-6-(methylamino)-

2-nitropyridine, 3-amino-6-(methyl-amino)-2-nitropyridine, 6-(ethylamino)-3-((2-hydroxyethyl)amino)-2-nitropyridine, 1,2,3,4-Tetrahydro-6-nitroquinoxaline, 7-Amino-3,4-dihydro-6-nitro-2H-1,4-benzoxazine (HC Red No. 14), 1-amino-2-[(2-hydroxyethyl)amino]-5-nitro-benzene (HC Yellow No. 5), 1-(2-hydroxyethoxy)-2-[(2-hydroxyethyl) amino]-5-nitrobenzene (HC Yellow No. 4), 1-[(2-hydroxyethyl)-amino]-2-nitrobenzene (HC Yellow No. 2), 2-(di(2-hydroxyethyl)amino)-5-nitrophenol, 2-[(2-hydroxyethyl)-amino]-1-methoxy-5-nitrobenzene, 2-amino-3-nitrophenol, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)amino]-4-nitrobenzene, 4-[(2,3-dihydroxypropyl)amino]-3-nitro-1-trifluormethyl-benzene (HC Yellow No. 6), 1-chloro-2,4-bis-[(2-hydroxyethyl)-amino]-5-nitrobenzene (HC Yellow No. 10), 1-amino-4-((2-aminoethyl)amino)-5-methyl-2-nitrobenzene, 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluormethyl benzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 3-((2-hydroxyethyl)amino)4-methyl-1-nitrobenzene and 4-chloro-3-((2-hydroxyethyl)amino)-1-nitrobenzene.

Suitable examples of quinone dye compounds include 1,4-di-[(2,3-dihydroxypropyl)amino]-9,10-anthraquinone, 1-[(2-hydroxyethyl)amino]-4-methylamino-9,10-anthraquinone (Cl 61505, Disperse Blue No. 3), 2-[(2-Aminoethyl)amino]-9,10-anthraquinone (HC Orange No. 5), 1-hydroxy-4-[(4-methyl-2-sulfophenyl)amino]-9,10-anthraquinone, 1-[(3-aminopropyl)amino]-4-methylamino-9,10-anthraquinone (HC Blue No. 8), 1-[(3-aminopropyl) amino]-9,10-anthraquinone (HC Red No. 8), 1,4-diamino-2-methoxy-9,10-anthra-quinone (Cl 62015, Disperse Red No. 11, Solvent Violet No. 26), 1,4-dihydroxy-5,8-bis-[(2-hydroxyethyl)amino]-9,10-anthraquinone and (Cl 62500, Disperse Blue No. 7, Solvent Blue No. 69).

Suitable examples of basic dye compounds include 9-(dimethylamino)-benzo[a]phenoxazin-7-ium-chloride (Cl 51175; Basic Blue No. 6), di[4-(diethyl-amino)phenyl][4-(ethylamino)naphthyl]carbenium chloride (Cl 42595; Basic Blue No. 7), di-(4-(dimethylamino)phenyl)-(4-(methylphenylamino)naphthalen-1-yl)carbenium chloride (Cl 42563; Basic Blue No. 8), 3,7-di(dimethylamino)-phenothiazin-5-ium chloride (Cl 52015; Basic Blue No. 9), di[4-(dimethylamino)-phenyl][4-(phenylamino)naphthyl] carbenium chloride (Cl 44045; Basic Blue No. 26), 2-[(4-(ethyl(2-hydroxyethyl)amino)phenyl)azo]-6-methoxy-3 -methyl-benzothiazolium methyl sulfate (Cl 11154; Basic Blue No. 41), 8-amino-2-bromo-5-hydroxy-4-imino-6-[(3-(trimethylammonio)phenyl)amino]-1(4H)-naphthalenon-chloride (Cl 56059; Basic Blue No. 99), bis-[4-(dimethylamino)phenyl][4-(methylamino)phenylcarbenium chloride (Cl 42535; Basic Violet No. 1), tris-[4-(dimethylamino)phenyl]carbenium chloride (Cl 42555; Basic Violet No. 3), 2-[3,6-(diethylamino) dibenzopyranium-9-yl]benzoic acid chloride (Cl 45170; Basic Violet No. 10), Di(4-aminophenyl)(4-amino-3-methylphenyl)-carbenium chloride (Cl 42510; Basic Violet No. 14), 1,3-bis-[(2,4-diamino-5-methyl-phenyl)azo]-3-methylbenzene (Cl 21010; Basic Brown No. 4), 1-[(4-amino-phenyl)azo]-7-(trimethylammonio)-2-naphthol chloride (Cl 12250; Basic Brown No. 16), 1-[(4-amino-2-nitrophenyl)azo]-7-(trimethylammonio)-2-naphthol-chloride (Basic Brown No. 17), 1-[(4-amino-3-nitrophenyl) azo]-7-(trimethylammonio)-2-naphthol chloride (Cl 12251; Basic Brown No. 17), 3,7-diamino-2,8-dimethyl-5-phenylphenazinium chloride (Cl 50240; Basic Red No. 2), 1,4-dimethyl-5-[(4-(dimethylamino)phenyl)azo]-1,2,4-triazolium chloride (Cl 11055; Basic Red No. 22), 2-hydroxy-1-[(2-methoxyphenyl)azo]-7-(trimethyl-ammonio)naphthalene chloride (Cl 12245; Basic Red No. 76), 2-[2-((2,4-dimethoxyphenyl)amino)ethenyl]-1,3,3-trimethyl-3H-indol-1-ium chloride (Cl 48055; Basic Yellow No. 11), 3-methyl-1-phenyl-4-[(3-(trimethylammonio)-phenyl)azo]-pyrazol-5-one chloride (Cl 12719; Basic Yellow No. 57), di(4-(dimethylamino)phenyl)iminomethane hydrochloride (Cl 41000; Basic Yellow No. 2), bis-[4-(diethylamino)phenyl]phenylcarbenium hydrogen sulfate (1:1) (Cl 42040; Basic Green No. 1) and di(4-(dimethylamino)phenyl)phenylmethanol (Cl 42000; Basic Green No. 4).

Suitable examples of neutral azo dye compounds include 1-[di-(2-hydroxyethyl)amino]-3-methyl-4-[(4-nitrophenyl) azo]-benzene (Cl 11210, Disperse Red No. 17), 4-[(4-aminophenyl)azo]-1-[di(2-hydroxyethyl)amino]-3-methylbenzene (HC Yellow No. 7), 2,6-diamino-3-[(pyridine-3-yl)azo]-pyridine and 2-((4-(acetylamino) phenyl)azo)-4-methylphenol (Cl 11855; Disperse Yellow No. 3).

Suitable examples of acidic dye compounds include 6-hydroxy-5-[(4-sulfophenyl)azo]-2-naphthalene sulfonic acid disodium salt (Cl 15985; Food Yellow No. 3; FD&C Yellow No. 6), 2,4-dinitro-1-naphthol-7-sulfonic acid sodium salt (Cl 10316; Acid Yellow No. 1; Food Yellow No. 1), 2-(indan-1,3-dion-2-yl)quinolin-x,x-sulfonic acid (mixture of mono and disulfonic acid) (Cl 47005; D&C Yellow No. 10; Food Yellow No. 13; Acid Yellow No. 3), 5-hydroxy-1-(4-sulfophenyl)4-[(4-sulfophenyl)azo]pyrazol-3-carboxylic acid trisodium salt (Cl 19140; Food Yellow No. 4; Acid Yellow No. 23), 9-(2-carboxyphenyl)-6-hydroxy-3H-xanthen-3-on (Cl 45350; Acid Yellow No. 73; D&C Yellow No. 8), 4-((4-amino-3-sulfophenyl)azo) benzosulfonic acid disodium salt (Cl 13015, Acid Yellow No. 9), 5-[(2,4-dinitrophenyl)amino]-2-phenylaminobenzosulfonic acid sodium salt (Cl 10385; Acid Orange No. 3), 4-[(2,4-dihydroxyphenyl)azo]-benzosulfonic acid monosodium salt (Cl 14270; Acid Orange No. 6), 4-[(2-hydroxynaphth-1-yl)azo] benzosulfonic acid sodium salt (Cl 15510; Acid Orange No. 7), 4-[(2,4-dihydroxy-3-[(2,4-dimethylphenyl)azo]phenyl) azo]-benzosulfonic acid sodium salt (Cl 20170; Acid Orange No. 24), 4-hydroxy-3-[(4-sulfonaphth-1-yl)azo]-1-naphthalene sulfonic acid disodium salt (Cl 14720; Acid Red No. 14), 6-hydroxy-5-[(4-sulfonaphth-1-yl)azo]-2,4-naphthalene disulfonic acid trisodium salt (Cl 16255; Ponceau 4R; Acid Red No. 18), 3-hydroxy-4-[(4-sulfonaphth-1-yl)azo]-2,7-naphthalene disulfonic acid trisodium salt (Cl 16185; Acid Red No. 27), 8-amino-1-hydroxy-2-(phenylazo)-3,6-naphthalene disulfonic acid disodium salt (Cl 7200; Acid Red No. 33), 5-(acetylamino)-4-hydroxy-3-[(2-methyl-phenyl)azo]-2,7-naphthalene disulfonic acid disodium salt (Cl 18065; Acid Red No. 35), 2-(3-hydroxy-2,4,5,7-tetraiododibenzopyran-6-one-9-yl)-benzoic acid disodium salt (Cl 45430; Acid Red No. 51), N-[6-(diethylamino)-9-(2,4-disulfo-phenyl)-3H-xanthen-3-yliden]-N-ethylethanammonium hydroxide, inner salt, sodium salt (Cl 45100; Acid Red No. 52), 8-[(4-(Phenylazo) phenyl)azo]-7-naphthol-1,3-disulfonic acid sodium salt (Cl 27290; Acid Red No. 73), 2',41,51,7'-tetrabromo-3',6'- dihydroxyspiro[isobenzofuran-1(3H),9'-[9H]xanthen]-3-one disodium salt (Cl 45380; Acid Red No. 87), 2',4',5',7'-tetrabromo-4,5,6,7-tetrachloro-3',6'-dihydroxyspiro[isobenzofuran-1(3H), 9'[9H]xanthen]-3-one disodium salt (Cl 45410; Acid Red No. 92), 3',6'-dihydroxy-4',5'-diiodo-spiro[isobenzofuran-1(3H), 9'(9H)-xanthen]-3-one disodium salt (Cl 45425; Acid Red No. 95), 2-hydroxy-3-((2-hydroxynaphth-1-yl)azo)-5-nitrobenzene sulfonic acid monosodium salt (Cl 15685; Acid Red No. 184), (2-Sulfophenyl)-di-[4-(ethyl((4-sulfophenyl)methyl)amino)phenyl]carbenium disodium salt betaine (Cl 42090; Acid Blue No. 9; FD&C Blue No. 1), 1,4-bis-[(2-sulfo-4-methylphenyl)-amino]-9,10-anthraquinone disodium salt (Cl 61570; Acid Green No. 25), bis-[4-(dimethylamino)phenyl]-(3,7-disulfo-2-hydroxynaphth-1-yl)-carbenium inner salt, monosodium salt (Cl 44090; Food Green No. 4; Acid Green No. 50), bis-[4-(diethylamino)phenyl]-(2,4-disulfophenyl)carbenium inner salt, sodium salt (2:1) (Cl 42045; Food Blue No. 3; Acid Blue No. 1), bis-[4-(diethylamino)phenyl]-(5-hydroxy-2,4-disulfophenyl)carbenium inner salt, calcium salt (2:1) (Cl 42051; Acid Blue No. 3), 1-amino-4-(cyclohexylamino)-9,10-anthraquinone-2-sulfonic acid sodium salt (Cl 62045; Acid Blue No. 62), 2-(1,3-dihydro-3-oxo-5-sulfo-2H-indol-2-yliden)-2,3-dihydro-3-oxo-1H-indol-5-sulfonic acid disodium salt (Cl 73015; Acid Blue No. 74), 9-(2-carboxyphenyl)-3-[(2-methylphenyl)amino]-6-[(2-methyl-4-sulfophenyl)amino]xanthylium inner salt, monosodium salt (Cl 45190; Acid Violet No. 9), 1-hydroxy-4-[(4-methyl-2-sulfophenyl)amino]-9,10-anthraquinone sodium salt (Cl 60730; D&C Violet No. 2; Acid Violet No. 43), bis-[3-nitro-4-[(4-phenylamino)-3-sulfophenylamino]phenyl] sulfone (Cl 1041 0; Acid Brown No. 13), 5-amino-4-hydroxy-6-[(4-nitrophenyl)azo]-3-(phenylazo)-2,7-naphthalene disulfonic acid disodium salt (Cl 20470; Acid Black No. 1), 3-hydroxy-4-[(2hydroxynaphth-1-yl)azo]-7-nitro-1-naphthalen-sulfonic acid chromium complex (3:2) (Cl 15711; Acid Black No. 52), 3-[(2,4-dimethyl-5-sulfophenyl)azo]-4-hydroxy-1-naphthalene sulfonic acid disodium salt (Cl 14700; Food Red No. 1; Ponceau SX; FD&C Red No. 4), 4-(acetylamino)-5-hydroxy-6-[(7-sulfo-4-[(4-sulfophenyl)azo]naphth-1-yl)azo]-1,7-naphthalene disulfonic acid tetrasodium salt (Cl 28440; Food Black No. 1) and 3-hydroxy-4-(3-methyl-5-oxo-1-phenyl-4,5-dihydro-1H-pyrazol-4-yl-azo)-naphthalen-1-sulfonic acid sodium salt, chromium complex (Acid Red No. 195).

Additional suitable dye compounds include 4-((5-((2-hydroxyethyl)amino-1-methyl-1H-pyrazol-4-yl)-imino)-4,5-dihydro-5-((2-hydroxyethyl)imino)-1-methyl-1H-pyrazole monosulfate, 5-hydroxy-1,4-naphthoquinone (Cl 75500, Natural Brown No. 7), 2-hydroxy-1,4-naphthoquinone (Cl 75480, Natural Orange No. 6) and 1,2-dihydro-2-(1,3-dihydro-3-oxo-2H-indol-2yliden)-3H-indol-3-one (Cl 73000).

The embodiments of the hair dye composition according to the invention that also include the direct-dyeing dye compounds contain from 0.01 to 4 percent by weight of one or more of the above-named direct-dyeing dye compounds.

The compounds of formula (I) are not only suitable for dyeing keratin fibers, especially human hair, but also they can be used for dyeing of other natural fibers, for example cotton, jute, sisal, linen and silk; modified natural fibers, such as regenerate cellulose, nitrocellulose, alkyl cellulose or hydroxyalkyl cellulose or acetyl cellulose and synthetic fibers, such as polyamide fibers, polyurethane fibers or polyester fibers.

The form of the hair dye composition according to the invention can be, for example, a solution, especially an aqueous or aqueous-alcoholic solution, a cream, a gel, a surfactant-containing foam solution, (shampoo, aerosol), an emulsion or another water-containing carrier suitable for application to hair. The compositions of the invention comprise a mixture of dye ingredients with conventional additive ingredients suitable for this type of preparation.

Conventional additive ingredients in solutions, creams, emulsions or gels may be employed in the compositions of the invention. For example, these additive ingredients include water, lower aliphatic monohydric or polyhydric alcohols, for example, alkanols, especially with one to four carbon atoms, especially ethanol, propanol or isopropanol, butanol, isobutanol, dihydric and trihydric alcohols, especially those with 2 to 6 carbon atoms, for example, ethylene glycol, propylene glycol, 1,3-propandiol, 1,4-butandiol, 1,5-pentandiol, 1,6-hexandiol, 1,2,6-hexantriol, glycerol, diethylene glycol, dipropylene glycol, tripropylene glycol, polypropylene glycol, lower alkyl ethers of multihydric alcohols, such as ethylene glycol monomethyl ether or ethylene glycol monoethyl ether or ethylene glycol monopropyl ether or ethylene glycol monobutyl ether, diethylene glycol monomethyl ether or diethylene glycol monoethyl ether, triethylene glycol monomethyl ether or triethylene glycol monoethyl ether; ketones and keto alcohols, especially those with 3 to 7 carbon atoms, for example acetone, methyl ethyl ketone, diethyl ketone, methyl isobutyl ketone, methyl phenyl ketone, cyclopentanone, cyclohexanone and diacetone alcohol; ethers, such as ethyl formate, methyl formate, methyl acetate, ethyl acetate, propylene acetate, butyl acetate, phenyl acetate, ethylene glycol monoethyl ether acetate and acetic acid hydroxy ethyl ester, amides, such as dimethylformamide and dimethyl acetamide, N-methylpyrrolidone, as well as urea, tetramethylurea and thiodiglycol.

Furthermore the hair dye compositions according to the invention can also contain wetting agents and emulsifiers from the classes of anionic, cationic, amphoteric, nonionic or zwitterionic surface-active sugstances, for example fatty alcohol sulfates, alkane sulfonates, alkylbenzene sulfonates, alkyltrimethylammonium salts, alkylbetaines, α-olefin sulfates, ethoxylated fatty alcohols, ethoxylated nonylphenols, fatty acid alkanol amines, ethoxylated fatty acid ester, fatty alcohol polyglycol ether sulfates, alkylpolyglucosides; thickeners, such as higher fatty alcohols, starches, cellulose derivative compounds, Vaseline® (petrolatum), paraffin oils, fatty acids and other fatty ingredients in emulsion form, water-soluble polymer thickener ingredients, such as natural gums, guar gums, xanthan gums, St. Johns' wart meal, pectin dextran, agar-agar, amylose, amylopectin, dextrin, clay or completely synthetic hydrocolloids, such as polyvinyl alcohol; care ingredients, such as lanolin derivative compounds, cholesterol, pantothenic acid, water-soluble cationic polymers, protein derivative compounds, provitamins, vitamins, plant extracts, sugar and betaine; and auxiliary substances, such as moisturizers, electrolytes, antioxidants, fatty amides, sequestering agents, film-forming agents and preservative agents. Besides water the hair dyeing composition according to the invention can also contain water-soluble organic solvents or a mixture of those organic solvents or water/organic solvent mixture.

The above-mentioned additive ingredients are used in amounts suitable for their purposes, for example the wetting agents and emulsifiers are present in a concentration of about 0.5 to 30 percent by weight, the thickeners, in an amount of about 0.1 to 25 percent by weight and the care ingredients in an amount of about 0.1 to 5 percent by weight.

The dye composition according to the invention can react as a weak acid, a neutral media or a base according to its composition. Its pH can be adjusted in the acid range, preferably with citric acid, lactic acid, tartaric acid or phosphoric acid, while its pH can be adjusted in the basic or alkaline range, preferably with ammonia. However in the alkaline pH range the pH can also be adjusted with organic amines, such as monoethanolamine, diethanolamine, triethanolamine, N-methyl-N-ethanolamine, N-methyl-N,N-diethanolamine, 2-(2-hydroxyethoxy)-ethanolamine, di-2-(2-hydroxyethoxy)ethanamine and tri-2-(2-hydroxyethoxy)-ethanamine or inorganic bases, such as hydroxides, for example lithium hydroxide, sodium hydroxide and potassium hydroxide. Preferably the hair dye composition according to the invention has a pH of from 5 to 8.

When using a dye solution according to the invention for dyeing hair, the hair dye solution according to the invention is allowed to act on the hair for about 10 to 45 minutes at a temperature of from 20 to 50° C., preferably for 40 minutes at 40° C. Then it is rinsed from the hair with water and the hair is dried. If necessary the hair is washed with a shampoo in connection with this rinsing and/or after-rinsed with a weak organic acid. Subsequently the hair is dried.

The hair dye composition according to the invention provides dyed hair colors with outstanding fastness properties, especially light fastness, washing fastness and rubbing fastness. The great color intensities and color purity of the color shades and tones obtained are particularly noteworthy. Finally gray or chemically not pre-damaged hair may be dyed with the compositions according to the invention without any problems and with very good color coverage. The colors obtained are uniform and are very reproducible independently of the different structure of the hair.

The compounds of formula (I) can be produced by reaction of a suitable 1,3-indandione with malonic acid dinitrile. The general synthetic method is, described, for example, in the article by K. A. Bello, L. Cheng and J. Griffiths in J. Chem. Soc. Perkin Trans. II, p. 817 (1987).

The following examples should illustrate the invention in greater detail, but should not be considered as limiting the appended claims or the broad definition of the invention above.

EXAMPLES

I. Synthesis Examples

Example 1

Synthesis of 1,3-bis(dicyanomethylen)indane 0.08 mol of 1,3 indandione and 0.28 mol malonodinitrile are stirred into 200 ml ethanol at room temperature. After 15 minutes 0.12 mol sodium acetate trihydrate are added. The reaction mixture is heated for about 5 hours under reflux. After the termination of the reaction the reaction mixture is filtered, mixed with 400 ml water and adjusted to a pH of from 1 to 2 with hydrochloric acid. The precipitate is filtered, washed with water and then dried. The yield amounts to 85% of theoretical. The product has a melting point of 224 to 228° C.

| CHN Analysis: | | | |
|---|---|---|---|
| ($C_{15}H_5N_4$) | % C | % H | % N |
| calculated: | 74.37 | 2.50 | 23.13 |
| found: | 74.11 | 2.62 | 23.05 |

Example 2

Synthesis of 2-methyl-1,3-bis(dicyanomethylen)indane 0.04 mol 2-methyl-1,3-indandione and 0.12 mol malonodinitrile are stirred into 200 ml ethanol at room temperature. After 15 minutes 0.6 mol sodium acetate trihydrate are added. The reaction mixture is heated for about 5 hours under reflux. After the termination of the reaction the reaction mixture is filtered, mixed with 200 ml water and adjusted to a pH of from 1 to 2 with hydrochloric acid. The precipitate is filtered, washed with water and then dried.

Example 3

Synthesis of 2-phenyl-1,3-bis(dicyanomethylen)indane 0.04 mol 2-phenyl-1,3-indandione and 0.12 mol malonodinitrile are stirred into 200 ml ethanol at room temperature. After 15 minutes 0.6 mol sodium acetate trihydrate are added. The reaction mixture is heated for about 5 hours under reflux. After the termination of the reaction the reaction mixture is filtered, mixed with 200 ml water and adjusted to a pH of from 1 to 2 with hydrochloric acid. The precipitate is filtered, washed with water and then dried.

II. Examples of Hair Dye Compositions

Example 4: Hair Dye Composition

| | |
|---|---|
| 0.61 g | 1,3-bis(dicyanomethylen)indane |
| 10.00 g | isopropanol |
| 1.00 g | benzyl alcohol |
| 10.00 g | lauryl alcohol diglycol ether sulfate sodium salt (28% aqueous solution) |
| to 100.00 g | water |

The above ready-to-use hair dye composition is obtained by mixing dye compound ingredients with the remaining components immediately prior to use. The adjustment of the pH occurs either with lactic acid or with dilute ammonia solution. Bleached hair was then treated with the hair dye composition for 40 minutes at a temperature of 40° C. (once with an acid pH value obtained by adding with lactic acid and once with a basic pH value by adding ammonia solution). Subsequently the hair was rinsed with water and dried. The hair color for the dyeing both at a pH of 5 and at a pH of 8 is an intense blue.

Example 5: Hair Dye Composition

| | |
|---|---|
| 0.0015 g | 1,3-bis(dicyanomethylen)indane |
| 0.0600 g | 5-chloro-4-((2-hydroxyethyl)amino)-2-nitroaniline |

| Example 5: Hair Dye Composition | |
| --- | --- |
| 0.0250 g | 1-((4-amino-2-nitrophenyl)azo)-7-(trimethyl-ammonium)-2-naphthol chloride |
| 0.0300 g | 4-(di(2-hydroxyethyl)amino)-2-nitroaniline |
| 10.0000 g | ethanol |
| 10.0000 g | lauryl alcohol diglycol ether sulfate sodium salt (28% aqueous solution) |
| to 100.00 g | water |

The above ready-to-use hair dye composition is obtained by mixing dye compound ingredients with the remaining components immediately prior to use. The pH is adjusted to 8 with dilute ammonia solution. Bleached hair is then treated with the hair dye composition for 40 minutes at a temperature of 40° C. Subsequently the hair was rinsed with water and dried. The hair color obtained is blond.

| Example 6: Hair Dye Composition | |
| --- | --- |
| 0.5200 g | 1,3-bis(dicyanomethylen)indane |
| 0.2600 g | 4-(ethyl(2-hydroxyethyl)amino)-N-2-hydroxyethyl)-2-nitroaniline hydrocholoride |
| 0.0900 g | N-(2-hydroxyethyl)-4-methyl-2-nitroaniline |
| 0.0800 g | 5-chloro-4-((2,3-dihydroxypropyl)amino)-2-nitroaniline |
| 0.1700 g | 1-((4-amino-2-nitrophenyl)azo)-7-(trimethyl-ammonium)-2-naphthol chloride |
| 0.0160 g | di-(4-(diethylamino)phenyl)(4-(ethylamino)napththyl)-carbenium chloride |
| 10.0000 g | ethanol |
| 10.0000 g | lauryl alcohol diglycol ether sulfate sodium salt (28% aqueous solution) |
| to 100.00 g | water |

The above ready-to-use hair dye composition is obtained by mixing dye compound ingredients with the remaining components immediately prior to use. The pH is adjusted to 8 with dilute ammonia solution. Bleached hair is then treated with the hair dye composition for 40 minutes at a temperature of 40° C. Subsequently the hair was rinsed with water and dried. The hair color obtained is brown.

| Example 7: Hair Dye Composition | |
| --- | --- |
| 0.0020 g | 1,3-bis(dicyanomethylen)indane |
| 0.0005 g | di-(4-aminophenyl)(4-amino-3-methylphenyl)carbenium chloride |
| 10.00 g | isopropanol |
| 1.00 g | benzyl alcohol |
| 10.00 g | lauryl alcohol diglycol ether sulfate sodium salt (28% aqueous solution) |
| to 100.00 g | water |

The above ready-to-use hair dye composition is obtained by mixing dye compound ingredients with the remaining components immediately prior to use. The pH is adjusted either with lactic acid or with dilute ammonia solution. Bleached hair is then treated with the hair dye composition for 40 minutes at a temperature of 40° C. Subsequently the hair was rinsed with water and dried. The hair color obtained is silver gray.

| Example 8: Hair Dye Composition | |
| --- | --- |
| 0.65 g | 2-methyl-1,3-bis(dicyanomethylen)indane |
| 10.00 g | isopropanol |
| 1.00 g | benzyl alcohol |
| 10.00 g | lauryl alcohol diglycol ether sulfate sodium salt (28% aqueous solution) |
| to 100.00 g | water |

The above ready-to-use hair dye composition is obtained by mixing dye compound ingredients with the remaining components immediately prior to use. The pH is adjusted either with lactic acid or with dilute ammonia solution. Bleached hair is then treated with the hair dye composition for 40 minutes at a temperature of 40° C. (once with an acid pH value obtained by adding with lactic acid and once with a basic pH value by adding ammonia solution). Subsequently the hair was rinsed with water and dried. The hair color obtained at both a pH of 5 and 8 is an intense blue color.

| Example 9: Hair Dye Composition | |
| --- | --- |
| 0.80 g | 2-phenyl-1,3-bis(dicyanomethylen)indane |
| 10.00 g | isopropanol |
| 1.00 g | benzyl alcohol |
| 10.00 g | lauryl alcohol diglycol ether sulfate sodium salt (28% aqueous solution) |
| to 100.00 g | water |

The above ready-to-use hair dye composition is obtained by mixing dye compound ingredients with the remaining components immediately prior to use. The pH is adjusted either with lactic acid or with dilute ammonia solution. Bleached hair is then treated with the hair dye composition for 40 minutes at a temperature of 40° C. (once with an acid pH value obtained by adding with lactic acid and once with a basic pH value by adding ammonia solution). Subsequently the hair was rinsed with water and dried. The hair color obtained at both a pH of 5 and 8 is an intense blue color.

Unless otherwise indicated, all percentages are percentages by weight.

The disclosure in German Patent Application 198 52 337.8 of Nov. 13, 1998 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a dye composition containing 1,3-bis (dicyanomethylen)indane, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

We claim:

1. A composition for dyeing keratin fibers comprising water;

from 0.01 to 10 percent by weight of at least one indane derivative compound of formula (I), or a physiologically compatible, water-soluble salt thereof:

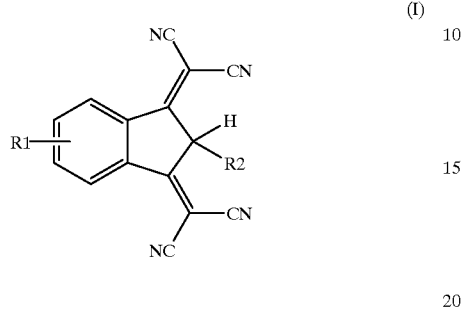

(I)

wherein R1 is hydrogen, a halogen atom, a cyano group, a hydroxy group, a $C_1$— to $C_4$— alkoxy group, a $C_1$— to $C_6$— alkyl group, a nitro group, an amino group, an alkylamino group, a dialkylamino group, a —C(O)H group, a —COOR3 group, a —SO2R3 or a —C(O)CH3 group, wherein R3 is hydrogen, phenyl or a $C_1$— to $C_6$— alkyl group; and wherein R2 is hydrogen, a $C_1$— to $C_6$— alkyl group or a phenyl group;

from 0.5 to 30 percent by weight of at least one wetting agent or emulsifier; and at least one additive ingredient selected from the group consisting of monohydric alcohols; polyhydric alcohols, ketones, keto alcohols, ethers, moisturizers, electrolytes, antioxidants, fatty amides, sequestering agents, film-forming agents, thickeners, care ingredients and preservative agents, wherein said at least one additive ingredient is present in a suitable amount for purposes thereof.

2. The composition as defined in claim 1, wherein said at least one indane derivative compound of formula (I) is selected from the group consisting of 1,3-bis(dicyanomethylen)indane, 2-methyl-1,3-bis(dicyanomethylen)indane and 2-phenyl-1,3-bis-(dicyanomethylen)indane.

3. The composition as defined in claim 1, further comprising at least one direct-dyeing dye compound selected from the group consisting of nitro dye compounds, azo dye compounds and quinone dye compounds.

4. The composition as defined in claim 3, containing from 0.01 to 4 percent by weight of said at least one direct-dyeing dye compound.

5. The composition as defined in claim 1, further comprising at least one direct-dyeing dye compound selected from the group consisting of basic dye compounds, acidic dye compounds and neutral dye compounds other than those of formula (I).

6. The composition as defined in claim 5, containing from 0.01 to 4 percent by weight of said at least one direct-dyeing dye compound.

7. The composition as defined in claim 1, shaving a pH of 5.0 to 8.0.

8. The composition as defined in claim 1, consisting of a hair dyeing composition.

9. A composition for dyeing keratin fibers, said composition having a pH of from 5.0 to 8.0 and comprising water;

from 0.01 to 10 percent by weight of at least one indane derivative compound of formula (I), or a physiologically compatible, water-soluble salt thereof:

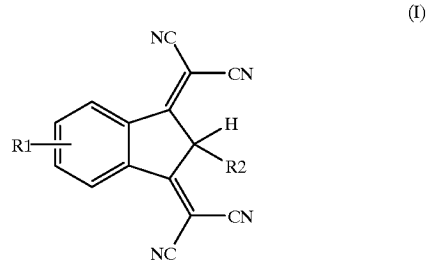

(I)

wherein R1 is hydrogen, a halogen atom, a cyano group, a hydroxy group, a $C_1$— to $C_4$— alkoxy group, a $C_1$— to $C_6$— alkyl group, a nitro group, an amino group, an alkylamino group, a dialkylamino group, a —C(O)H group, a —COOR3 group, a S02R3 or a —C(O)CH3 group, wherein R3 is hydrogen, phenyl or a $C_1$— to $C_6$— alkyl group; and R2 is hydrogen, a $C_1$— to $C_6$— alkyl group or a phenyl group;

from 0.01 to 4 percent by weight of at least one member selected from the group consisting of nitro dye compounds, azo dye compounds and quinone dye compounds; and at least one additive ingredient selected from the group consisting of monohydric alcohols, polyhydric alcohols, ketones, keto alcohols, ethers, wetting agents, emulsifiers, thickeners, care ingredients, moisturizers, electrolytes, antioxidants, fatty amides, sequestering agents, film-forming agents and preservative agents, wherein said at least one additive ingredient is present in a suitable amount for purposes thereof.

10. A composition for dyeing keratin fibers, said composition having a pH of from 5.0 to 8.0 and comprising water;

from 0.01 to 10 percent by weight of at least one indane derivative compound of formula (I), or a physiologically compatible, water-soluble salt thereof:

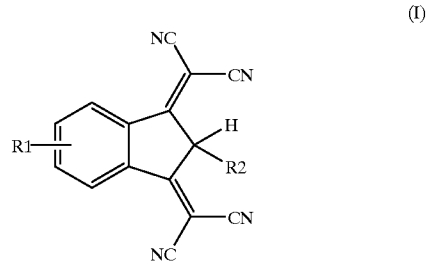

(I)

wherein R1 is hydrogen, a halogen atom, a cyano group, a hydroxy group, a $C_1$— to $C_4$— alkoxy group, a $C_1$— to $C_6$— alkyl group, a nitro group, an amino group, an alkylamino group, a dialkylamino group, a —C(O)H group, a —COOR3 group, a S02R3 or a —C(O)CH3 group, wherein R3 is hydrogen, phenyl or a $C_1$— to $C_6$— alkyl group; and R2 is hydrogen, a $C_1$— to $C_6$— alkyl group or a phenyl group;

from 0.01 to 4 percent by weight of at least one member selected from the group consisting of basic dye compounds, acidic dye compounds and neutral dye compounds other than those of formula (I); and at least one additive ingredient selected from the group consisting of monohydric alcohols, polyhydric alcohols, ketones, keto alcohols, ethers, wetting agents, emulsifiers, thickeners, care ingredients, moisturizers, electrolytes, antioxidants, fatty amides, sequestering agents, film-forming agents and preservative agents, wherein said at least one additive ingredient is present in a suitable amount for purposes thereof.

11. A method of dyeing hair, said method comprising the steps of:

a) applying a hair dye composition to the hair;

b) after the applying of step a), allowing the hair dye composition to remain on the hair for an acting time of from 10 to 45 minutes at a temperature of from 20 to 50° C.;

c) after the allowing of step b), rinsing the hair dye composition from the hair with water; and d) drying the hair;

wherein the hair dye composition comprises water; from 0.01 to 10 percent by weight of at least one indane derivative compound of formula (I), or a physiologically compatible, water-soluble salt thereof:

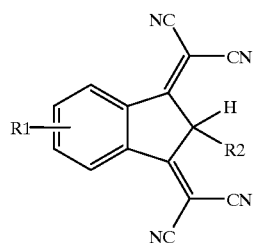

(I)

wherein R1 is hydrogen, a halogen atom, a cyano group, a hydroxy group, a $C_1$— to $C_4$— alkoxy group, a $C_1$— to $C_6$— alkyl group, a nitro group, an amino group, an alkylamino group, a dialkylamino group, a —C(O)H group, a —COOR3 group, a —SO2R3 or a —C(O)CH3 group, wherein R3 is hydrogen, phenyl or a $C_1$— to $C_6$— alkyl group; and wherein R2 is hydrogen, a $C_1$— to $C_6$— alkyl group or a phenyl group;

from 0.5 to 30 percent by weight of at least one wetting agent or emulsifier; and at least one additive ingredient suitable for the hair dyeing composition and selected from the group consisting of monohydric alcohols; polyhydric alcohols, ketones, keto alcohols, ethers, moisturizers, electrolytes, antioxidants, fatty amides, sequestering agents, film-forming agents, thickeners, hair care ingredients and preservative agents, wherein said at least one additive ingredient is present in a suitable amount for purposes thereof.

12. A method of dyeing hair, said method comprising the steps of:

a) applying a hair dye composition to the hair;

b) after the applying of step a), allowing the hair dye composition to remain on the hair for an acting time of from 10 to 45 minutes at a temperature of from 20 to 50° C.;

c) after the allowing of step b), rinsing the hair dye composition from the hair with water; and d) drying the hair;

wherein the hair dye composition comprises water; from 0.01 to 10 percent by weight of at least one indane derivative compound of formula (I), or a physiologically compatible, water-soluble salt thereof:

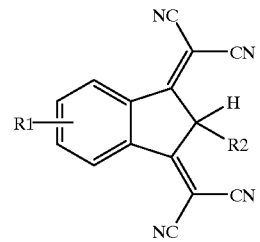

(I)

wherein R1 is hydrogen, a halogen atom, a cyano group, a hydroxy group, a $C_1$— to $C_4$— alkoxy group, a $C_1$— to $C_6$— alkyl group, a nitro group, an amino group, an alkylamino group, a dialkylamino group, a —C(O)H group, a —COOR3 group, a —SO2R3 or a —C(O)CH3 group, wherein R3 is hydrogen, phenyl or a $C_1$— to $C_6$— alkyl group; and wherein R2 is hydrogen, a $C_1$— to $C_6$— alkyl group or a phenyl group;

from 0.01 to 4 percent by weight of at least one member selected from the group consisting of nitro dye compounds, azo dye compounds and quinone dye compounds; and at least one additive ingredient suitable for the hair dyeing composition selected from the group consisting of monohydric alcohols, polyhydric alcohols, ketones, keto alcohols, ethers, wetting agents, emulsifiers, thickeners, care ingredients, moisturizers, electrolytes, antioxidants, fatty amides, sequestering agents, film-forming agents and preservative agents, wherein said at least one additive ingredient is present in a suitable amount for purposes thereof.

13. A method of dyeing hair, said method comprising the steps of:

a) applying a hair dye composition to the hair;

b) after the applying of step a), allowing the hair dye composition to remain on the hair for an acting time of from 10 to 45 minutes at a temperature of from 20 to 50° C.;

c) after the allowing of step b), rinsing the hair dye composition from the hair with water; and d) drying the hair;

wherein the hair dye composition comprises water;

from 0.01 to 10 percent by weight of at least one indane derivative compound of formula (I), or a physiologically compatible, water-soluble salt thereof:

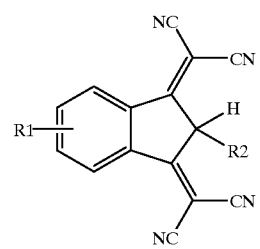

(I)

wherein R1 is hydrogen, a halogen atom, a cyano group, a hydroxy group, a $C_1$— to $C_4$— alkoxy group, a $C_1$— to $C_6$— alkyl group, a nitro group, an amino group, an alkylamino group, a dialkylamino group, a —C(O)H group, a —COOR3 group, a —SO2R3 or a —C(O)CH3 group, wherein R3 is hydrogen, phenyl or a $C_1$— to $C_6$— alkyl group; and wherein R2 is hydrogen, a $C_1$— to $C_6$— alkyl group or a phenyl group;

from 0.01 to 4 percent by weight of at least one member selected from the group consisting of basic dye compounds, acidic dye compounds and neutral dye compounds other than those of formula (I); and at least one additive ingredient suitable for the hair dyeing composition and selected from the group consisting of monohydric alcohols, polyhydric alcohols, ketones, keto alcohols, ethers, wetting agents, emulsifiers, thickeners, hair care ingredients, moisturizers, electrolytes, antioxidants, fatty amides, sequestering agents, film-forming agents and preservative agents, wherein said at least one additive ingredient is present in a suitable amount for purposes thereof.

* * * * *